United States Patent [19]
Munden et al.

[11] 3,979,951
[45] Sept. 14, 1976

[54] TESTING FABRIC SEWING PROPERTIES

[76] Inventors: Dennis Lawrence Munden, 18, Adel Towers Court, Leeds 16; Carol Anne Leeming, 9, Winfield Grove, Leeds 2, both of Yorkshire, England

[22] Filed: Oct. 25, 1974

[21] Appl. No.: 518,073

[30] Foreign Application Priority Data
Oct. 27, 1973 United Kingdom............... 50291/73

[52] U.S. Cl..................................... 73/159; 73/81
[51] Int. Cl.²...................... G01L 5/00; G01N 3/00
[58] Field of Search .................... 73/159, 81; 26/70; 73/102, 7

[56] References Cited
UNITED STATES PATENTS

| | | | |
|---|---|---|---|
| 3,026,726 | 3/1962 | Reading............................... | 73/159 |
| 3,541,843 | 11/1970 | Flesher ................................ | 73/159 |
| 3,732,727 | 5/1973 | Hinnergarot et al.................... | 73/81 |

*Primary Examiner*—Richard C. Queisser
*Assistant Examiner*—Joseph W. Roskos
*Attorney, Agent, or Firm*—Oblon, Fisher, Spivak, McClelland & Maier

[57] ABSTRACT

A fabric is tested for its sewability — its likelihood of suffering seam damage during making-up into garments or other textile articles — by an instrument which effects or attempts needle penetration simulating a machine sewing operation and indicates the incidence of excessive penetration forces.

13 Claims, 4 Drawing Figures

3,979,951

TESTING FABRIC SEWING PROPERTIES

This invention relates to the testing of fabric sewing properties.

BACKGROUND TO THE INVENTION

Fabrics, by virtue of their construction, the material of which their fibres or threads are made, or their finish, have different degrees of resistance to penetration by a sewing needle. Knitted fabrics, of which increasing use is being made, are particularly prone to sewing defects caused by needle damage (see "Sewability of Knitted Fabrics" by Carol A. Leeming and D. L. Munden, Clothing Research Journal Vol. 1 No. 2 1973, The Clothing Institute, London). It sometimes happens that a batch of fabric is especially difficult to sew, which results in considerable wastage through faulty sewing, or possibly an expensive re-processing of the fabric. Testing the fabric before purchase, or, by the fabric producer during production, can avoid expensive mistakes.

SUMMARY OF THE INVENTION

The invention provides apparatus for testing fabric sewing properties comprising a fabric support and a needle holder relatively movable to effect or attempt needle penetration at a plurality of spaced apart points on the fabric, and indicating means for indicating resistance to penetration.

The indicating means may give a signal continuously varying with the force required to penetrate the fabric, and may comprise a strain gauge. It may be arranged that only excessive penetration forces are indicated — these may be counted, out of a number of insertions (or insertion attempts) and expressed as a ratio; the larger the ratio, the more difficult is the fabric to sew.

The apparatus may comprise threshold selector means to select the level above which penetration forces are indicated.

The apparatus may comprise counter means adapted to count the number of excessive penetration forces in a series of needle insertions or attempted needle insertions.

The apparatus may also comprise counter means to count the total number of needle insertions or attempted insertions, and further counting switch means adapted to effect a predetermined number of needle insertions or attempts in a fabric test sequence. Said latter counting switch means may be presettable to effect different predetermined numbers of needle insertions or attempts, in fabric test sequences for different fabrics or purposes.

The apparatus may comprise a needle holder adapted releasably to hold exchangeable needles.

The apparatus may comprise fabric feeding means adapted to feed a fabric past a needle position during a sequence of needle insertions or attempts. A single drive motor may effect needle insertion and fabric feeding. The single drive motor may be connected to a reduction gear box with a double-ended output shaft, one end of which effects needle penetration and the other end of which effects fabric feeding.

A needle holder may comprise a block slidable on parallel rods and reciprocable by a crank engaging a slot in the block.

The apparatus may comprise a fabric feed arrangement having a pair of cooperating rollers at least one of which is driven in steps to advance the fabric by an amount roughly equal to the length of a typical sewing machine stitch. Said driven roller may be mounted on a shaft supported at at least one end in a first unidirectional clutch preventing return motion of said shaft and a small amplitude angularly oscillating arm member driven at one end by an eccentric is mounted at its other end on the said shaft by a second unidirectional clutch arranged for motion transmission in the opposite sense to that of said first clutch.

Preferably, the generally advancing fabric undergoes a series of needle penetrations or attempts while being held stationary or substantially stationary during each penetration or attempt.

The apparatus may comprise a fabric presser plate resiliently urged towards a bed plate, both having aligned bores for passage of the needle.

Excessive penetration forces may be detected by electronic means emitting an indicating or counting pulse when a strain gauge signal exceeds a given value.

Excessive forces may be detected by a microswitch or like-acting device being actuated by displacement of a fabric presser plate due to an unsuccessful penetration attempt.

BRIEF DESCRIPTION OF THE DRAWINGS

Embodiments of apparatus for testing fabric sewing properties according to the invention will now be described with reference to the accompanying drawings in which.

DESCRIPTION OF THE PREFERRED EMBODIMENTS

Figure 1:
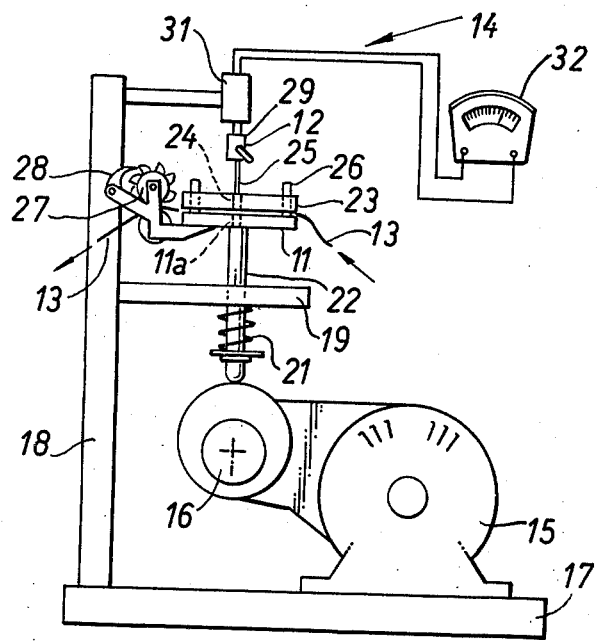
FIG. 1 is an elevation of one embodiment.
Figure 2:
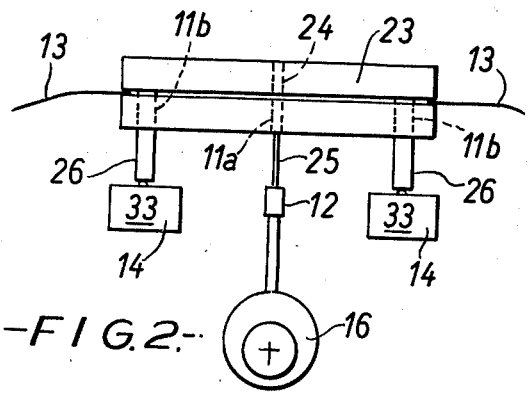
FIG. 2 is an elevation of another embodiment.

The apparatus for testing fabric sewing properties illustrated in FIGS. 1 and 2 comprises a fabric support 11 (with a needle hole 11a) and a needle head 12 relatively movable to effect or attempt needle penetration at a plurality of spaced apart points on the fabric 13 in the support 11, and indicating means 14 for indicating resistance to penetration.

The apparatus illustrated in FIG. 1 has an eccentric 16 driven by a motor 15 mounted on a base 17. A stand 18 rising from the base 17 has a platform 19 in which the fabric support 11 is mounted for vertical reciprocation against a return spring 21 on a rod 22 lifted by the eccentric 16. A plate 23 with a hole 24 for the needle 25 is guided on pillars 26 upstanding from the support 11. The plate 23 rests on the fabric 13 and serves not only as a guide for the needle, but also brakes the fabric 13 against a withdrawing roller arrangement 27 driven by a ratchet and pawl picking mechanism 28 stepped by a connecting rod from the vertical reciprocation of the fabric support 11. The needle 25 is mounted in a chuck or needle clamp 29 on a strain gauge 31 (of any desired type, for example a piezo-electric type) connected to a meter 32 indicating the force on the needle as it penetrates the fabric 13.

Clearly, any desired manner of calibration and any desired type of indicating meter can be used. Especially useful is a counting arrangement which counts the number of excessive forces (as determined by a pre-settable discriminator) and expresses this as a ratio of the total number of insertions.

The embodiment illustrated in FIG. 2 avoids the use of a strain gauge, and may be preferred as a more robust, if perhaps less sensitive device for general mill use. In this arrangement the fabric support 11 is a fixed plate, and the needle 25 is reciprocated on the needle head 12 upwardly through the needle hole 11a. The heavy plate 23, as before, rests on the fabric 13 in the support 11. In this case, however, the pillars 26 are fixed to the plate 23 and project through apertures 11b in the support 11 to contact microswitches 33. When the needle encounters excessive resistance to penetration, the point of the needle, instead of penetrating the fabric 13 and entering the needle hole 24, lifts fabric 13 and plate 23 so that at least one pillar 26 is lifted off its microswitch 33, which actuates an alarm or effects a counting operation. The weight of the plate 23 is chosen in accordance with the type of fabric under test. The fabric is forwarded as in the embodiment illustrated in FIG. 1 or in any other desired manner.

Figure 3:
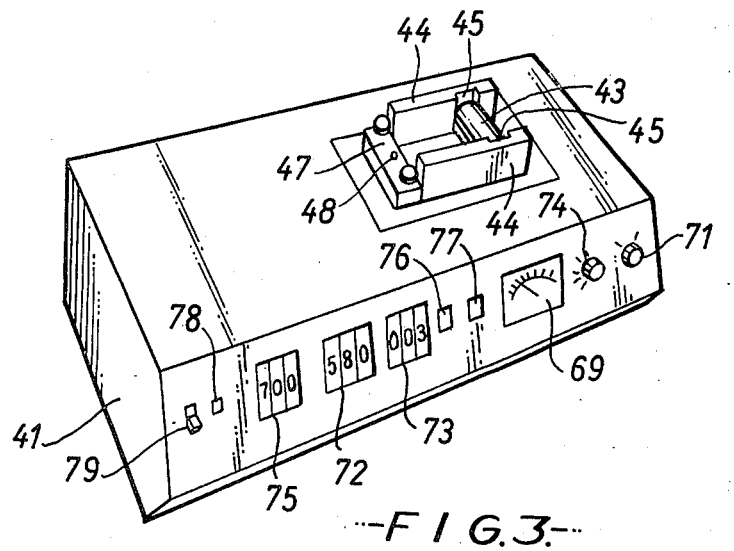
FIG. 3 is a perspective view of a further embodiment.
Figure 4:
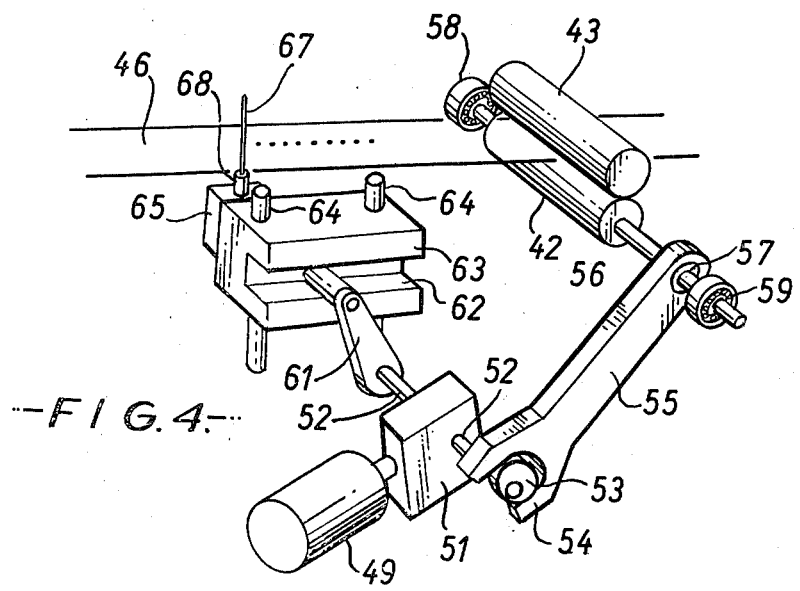
FIG. 4 is a view of a detail of the embodiment illustrated in FIG. 3.

FIGS. 3 and 4 illustrate a form of sewability tester which is particularly well adapted to laboratory or general mill use. The instrument is contained in a case 41, on a flat, upper surface of which is a fabric drive roller 42 (FIG. 4) and a bail roller 43 which is held between side guide plates 44 and is easily raisable in guide grooves 45 to permit the fabric 46 under test to be inserted. The roller 42 is mounted so as to drive the fabric from left to right as shown. The fabric is passed under a spring loaded presser plate 47 with a hole 48 for the needle. The drive for the needle, which is all located directly beneath the aforementioned flat upper surface of the case 41, is illustrated in FIG. 4. An electric motor 49 has a reduction gear box 51 with a double ended output shaft 52. On one end is an arm 55 which is connected to a shaft 56 supporting the drive roller 42 by a unidirectional clutch 57. The shaft 56 is supported in a ball bearing 58 at one end and, at the other end, in another unidirectional clutch 59. The clutches 57, 59 are arranged so that the shaft is turned, by the rocking motion of the arm 55, intermittently in the desired fabric drive direction.

The other end of the output shaft 52 carries a crank 61 which engages in a slot 62 of a block 63 vertically slidable on fixed rails 64. The block 63 carries a strain gauge 65 which carries the needle mount 68 holding the needle 67.

The strain gauge output, after amplification, is indicated on the meter 69. A socket may be provided by which this output can be connected to an oscilloscope or pen recorder. The meter sensitivity may be selected by a ranging switch 71, which may provide for two ranges, say, giving full scale deflection on the meter for 500 grams and 250 grams needle force respectively.

In addition, two counters 72, 73 are provided. Counter 72 is actuated to count the number of needle insertions or insertion attempts, or the number of revolutions of the output shaft 52. Counter 73 is actuated only by signals from the strain gauge above a predetermined threshold value, preselectable by a switch 74 which may provide, say, 10 threshold levels between 50 grams and 500 grams.

A decade switch 75 is presettable to count down the number of insertion attempts and switch off the drive when the pre-set number has been reached. Drive is started by switch 76 and may be interrupted if desired by stop switch 77. A neon indicator shows the condition of power supply switch 79.

With proper initial adjustment, the instrument can be used to provide a very sensitive test of the sewability of a fabric, in which the distinction between a fabric which can be sewn without damage and one which will suffer seam damage can be clearly seen.

We claim:

1. Apparatus for testing fabric sewing properties comprising:
   a fabric support;
   needle holding means, said support and said holding means being relatively movable;
   means to effect relative movement of said support and said holding means to effect a plurality of needle penetrations of a test fabric in said support at spaced apart points in said test fabric;
   discriminating means sensing single needle penetration forces in excess of a predetermined threshold level; and
   indicating means for indicating the number of penetrations in which excessive penetration force was encountered relative to the total number of penetrations effected,
   whereby the ratio, of the number of penetrations exhibiting an excessive force with respect to the total number of penetrations effected, is indicative of the sewability of the fabric, high ratio values thereby being indicative of fabrics which are difficult to sew.

2. Apparatus as claimed in claim 1, comprising
   f. strain gauge penetrating force sensing means.

3. Apparatus as claimed in claim 1, comprising
   g. first counter means indicating total number of penetration attempts, and
   h. second counter means indicating the number of penetration attempts at above-threshold force level.

4. Apparatus as claimed in claim 1, comprising
   i. counting switch means halting further needle penetration attempts after a predetermined number thereof.

5. Apparatus as claimed in claim 1, in which said counting switch means are presettable for setting different predetermined numbers of penetration attempts.

6. Apparatus as claimed in claim 1, comprising
   j. penetration force level indicating means.

7. Apparatus as claimed in claim 1, comprising
   k. a socket outlet for external indicating and external recodeing means.

8. Apparatus as claimed in claim 1, comprising
   l. an electric motor
   m. fabric feed means
   n. needle holder reciprocating means, and
   o. drive transmission means connecting said motor to said fabric feed means and said needle holder reciprocating means.

9. Apparatus as claimed in claim 1, said drive transmission means comprising
   p. a reduction gear having a double ended output shaft.

10. Apparatus as claimed in claim 1, comprising
    q. intermittent fabric feed means so arranged that fabric motion is substantially arrested during each penetration attempt.

11. A method for testing fabric sewing properties comprising the steps of:

penetrating a test fabric at a predetermined number of spaced apart points with a needle;

measuring the penetration force encountered for each penetration;

discriminating between penetration forces in excess of and below a predetermined threshold level; and counting the number of penetrations, out of said predetermined number, in which excessive penetration forces were encountered, whereby the ratio of the number of penetrations exhibiting an excessive force with respect to said predetermined number of penetrations effected, is indicative of the sewability of the fabric, high ratio values thereby being indicative of fabrics which are difficult to sew.

12. A method according to claim 11, wherein said predetermined number is from 100 to 900 inclusive.

13. A method according to claim 11, wherein said predetermined threshold level is from 50 to 500 grams.

* * * * *